US00PP33896P2

(12) United States Plant Patent
Lyrene et al.

(10) Patent No.: US PP33,896 P2
(45) Date of Patent: Jan. 25, 2022

(54) BLUEBERRY PLANT NAMED 'SENTINEL'

(50) Latin Name: ***Vaccinium corymbosum* L.**
Varietal Denomination: Sentinel

(71) Applicant: Florida Foundation Seed Producers, Inc., Marianna, FL (US)

(72) Inventors: Paul M. Lyrene, Micanopy, FL (US); James W. Olmstead, Aptos, CA (US)

(73) Assignee: FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 17/064,583

(22) Filed: Oct. 6, 2020

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

PP12,165 P2 10/2001 Lyrene
PP19,233 P2 9/2008 Lyrene

*Primary Examiner* — Kent L Bell
(74) *Attorney, Agent, or Firm* — Dentons US LLP

(57) ABSTRACT

'Sentinel' is a new and distinct southern highbush blueberry (*Vaccinium corymbosum* L.) variety distinguished at least by a low chilling requirement, vigorous, semi-upright to spreading growth habit, high early yield, good field disease resistance, and large fruit that are sweet and exhibit small, dry picking scars.

5 Drawing Sheets

Latin name of the genus and species of the plant claimed: *Vaccinium corymbosum* L.

Variety denomination: 'Sentinel'.

BACKGROUND OF THE INVENTION

The invention relates to a new and distinct hybrid variety of southern highbush blueberry (*Vaccinium corymbosum* L.) plant named 'Sentinel'. 'Sentinel' originated as a seedling that was generated from a cross performed in Gainesville, Fla. during February of 2008 between 'FL01-25' (unpatented), as the female (seed) parent, and 'Scintilla' (U.S. Plant Pat. No. 19,233 P2), as the male (pollen). The seedling was planted in a high-density field nursery in May of 2009, and the first fruit were evaluated in April of 2010. 'Sentinel' was first asexually propagated during 2011 by softwood stem cuttings in Gainesville, Fla. After the second year of fruiting in the field, 'Sentinel' was propagated by softwood stem cuttings during the spring of 2011 to establish an experimental 15-plant test plot for a variety test that was conducted during January of 2012 in Waldo, Fla. It was during this variety test that the experimental code 'FL11-155' was assigned. Based on the growth, yield and fruit quality of this plot, 'Sentinel' was repropagated by softwood stem cuttings and additional experimental test plots ranging from 5 to 45 plants were established for experimental research trials throughout Florida. These plots have been observed during flowering and ripening each year since establishment, and no mutations or off-type plants have been observed.

SUMMARY OF THE INVENTION

'Sentinel' differs from its parents and all other known southern highbush blueberry plants. The following are the most distinguishing characteristics of 'Sentinel' when grown under normal horticultural practices in Florida: (1) a low chilling requirement, particularly for the flower buds; (2) a vigorous, semi-upright to spreading growth habit; (3) early ripening (from late March through late April, when grown as a deciduous plant in north central Florida); (4) high yield and concentrated ripening; and (5) large, firm, sweet berries that exhibit small, dry picking scars.

'Sentinel' plants can be readily and unambiguously distinguished from those of its parents at least based upon earliness fruit yield. The early fruit yield exhibited by plants of 'Sentinel' is significantly earlier and higher than that of either 'FL01-25' and 'Scintilla'. Additionally, plants of 'Sentinel' are more vigorous than plants of 'Scintilla', and the fruit of 'Sentinel' is firmer than 'Scintilla'.

Blueberry variety 'Emerald' (U.S. Plant Pat. No. 12,165) is planted throughout the southeastern United States. Plants of 'Sentinel' and 'Emerald' can be readily and unambiguously distinguished at least based upon growth habit, the time at which their fruit is produced, and the fruit cluster tightness. Plants of 'Sentinel' display a more upright and vigorous growth habit than those of 'Emerald'. Plants of 'Sentinel' produce their fruit significantly earlier than those of 'Emerald' when no growth regulator is used, and the fruit cluster of 'Sentinel' are lose compared to the tight cluster of 'Emerald'.

BRIEF DESCRIPTION OF THE DRAWINGS

'Sentinel' is illustrated in the accompanying photographs, which show the plant's flowers, fruit, leaves, and form. Colors shown are as true as can be reasonably reproduced by photographic procedures and may differ from those cited in the detailed description, which accurately describe the colors of 'Sentinel'.

DETAILED BOTANICAL DESCRIPTION

Figure 1:
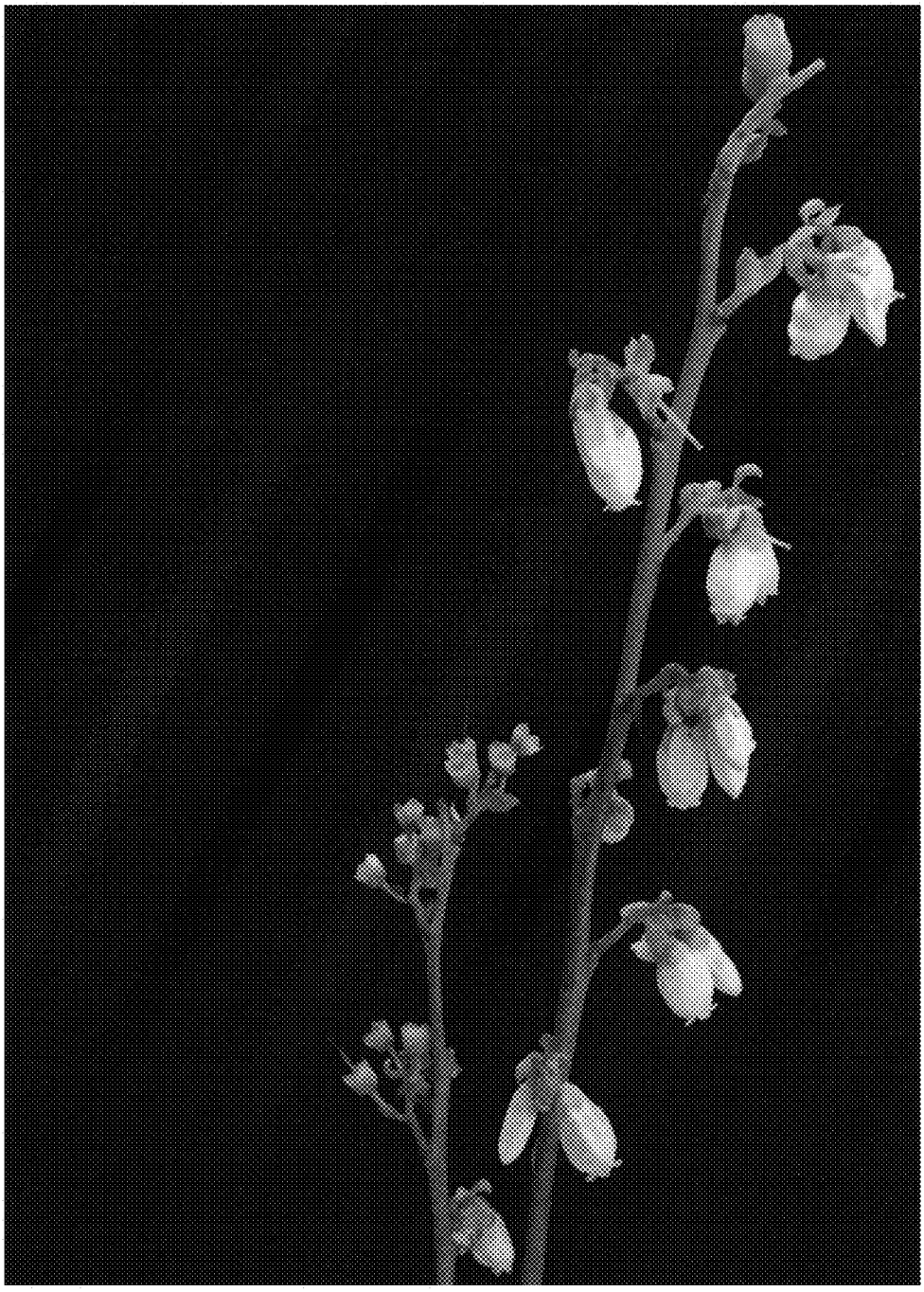
FIG. 1—Shows clusters of opening 'Sentinel' flowers.
Figure 2:
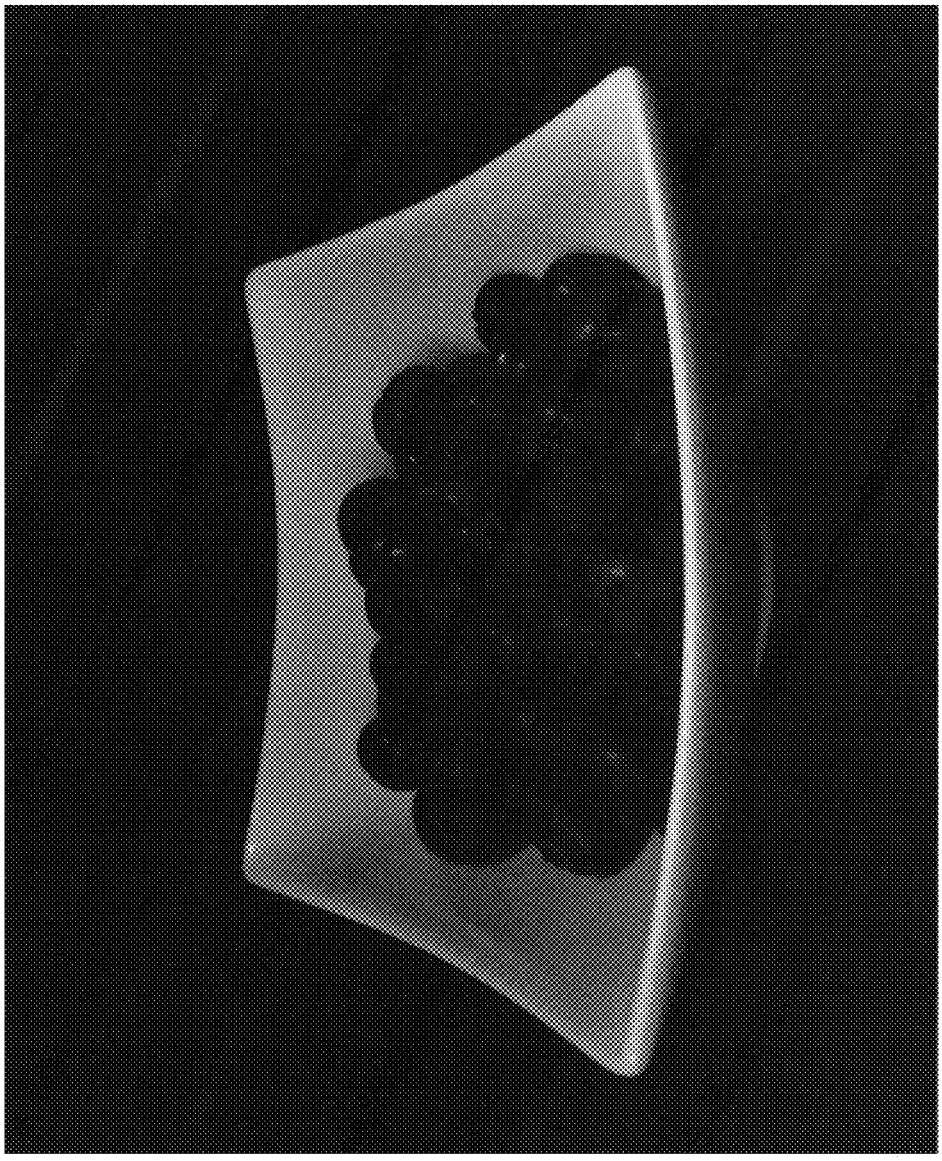
FIG. 2—Shows a close-up of harvested 'Sentinel' berries.
Figure 3:
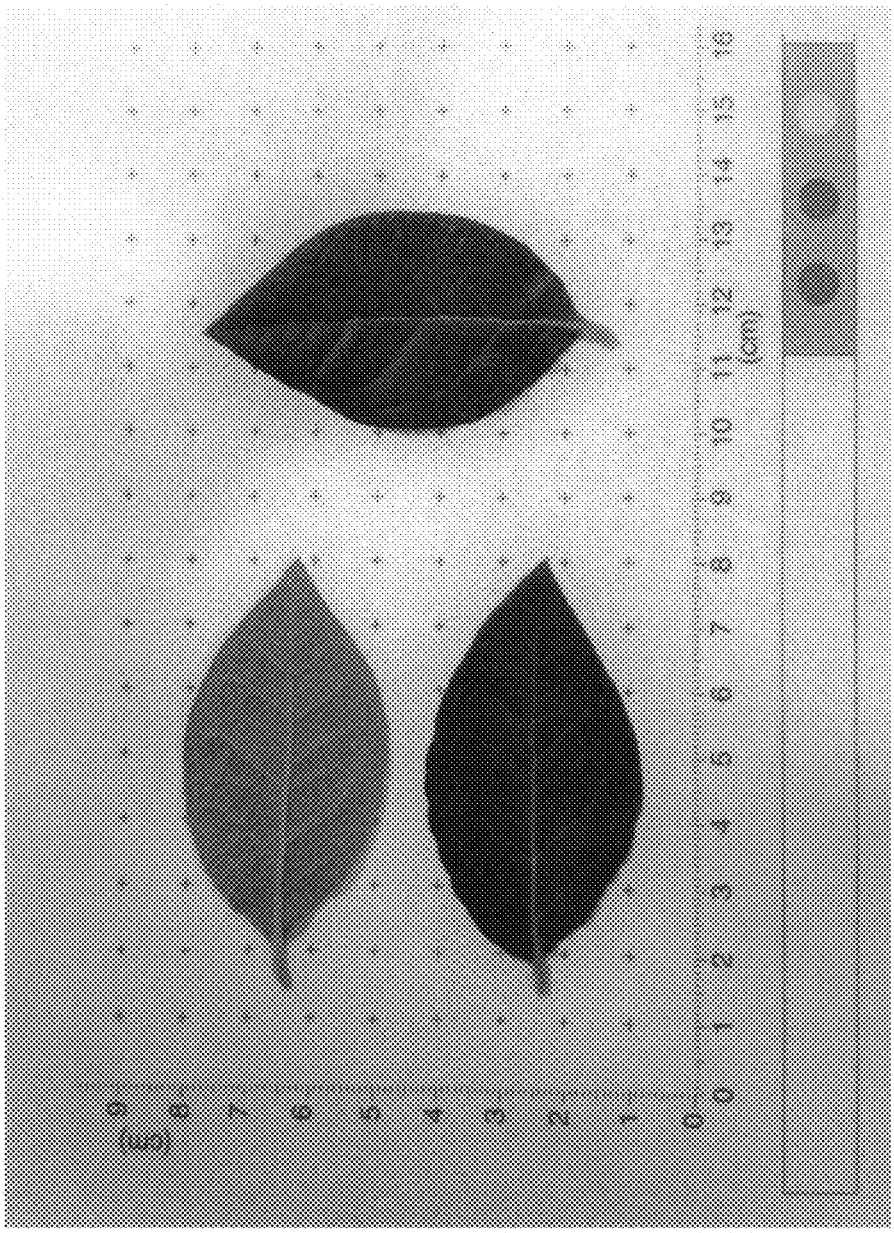
FIG. 3—Shows a close-up of mature 'Sentinel' leaves with a scale bar.
Figure 4:
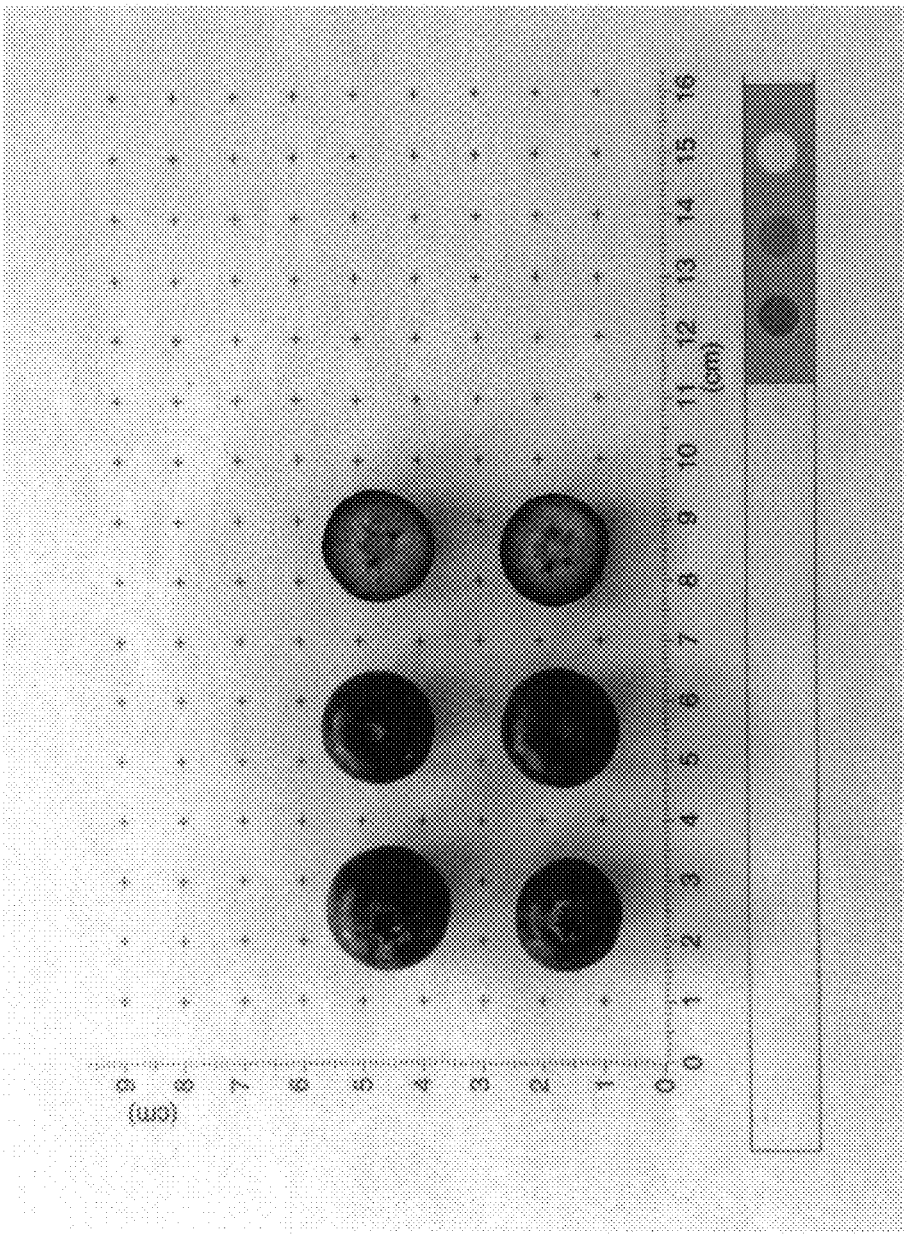
FIG. 4—Shows a close-up of mature 'Sentinel' fruit with a scale bar.
Figure 5:
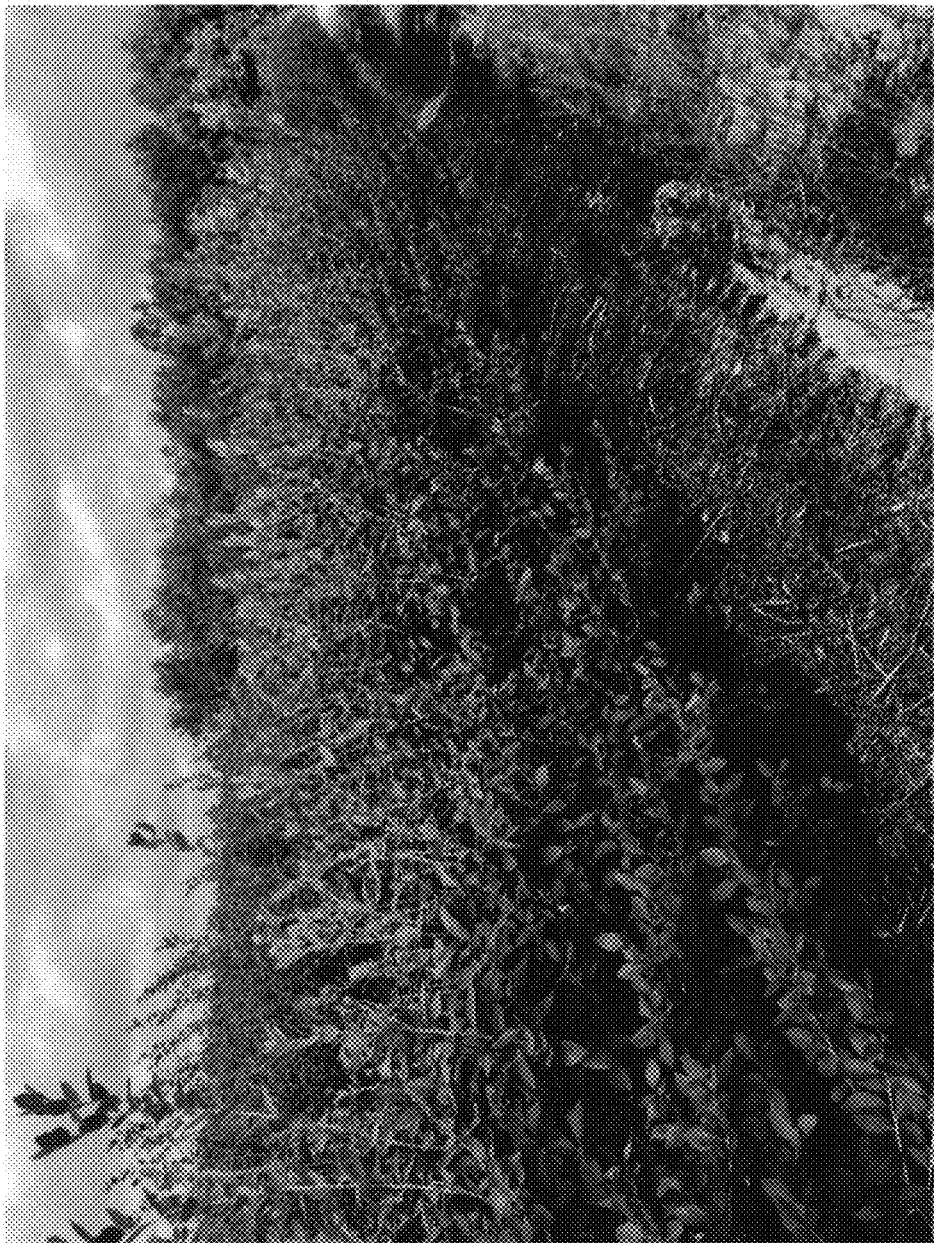
FIG. 5—Shows 5-year-old 'Sentinel' plants during the summer

The following detailed description sets forth distinctive characteristics of 'Sentinel'. The data that define these characteristics were collected from asexual reproductions carried out in Florida. The plant history was taken on a plot of plants growing in an experimental trial near Waldo, Fla. Certain characteristics may vary with plant age. The plant was 5 years of age when the data was collected unless otherwise indicated. 'Sentinel' has not been observed under all possible environmental conditions, and the measurements given may vary slightly when grown in different environments. Color descriptions are based on The Royal Horticultural Society (R.H.S.) Colour Chart by the Royal Horticultural Society, London, Sixth Edition, 2015. If any R.H.S. color designations below differ from the accompanying photographs, the R.H.S. color designations are accurate.

Classification:

*Family*.—Ericaceae.

*Botanical*.—*Vaccinium corymbosum* L.

*Common name*.—Southern Highbush Blueberry.

*Cultivar name*.—'Sentinel'.

Plant:

*Plant vigor*.—High.

*Growth habit*.—Semi-upright to Spreading.

*Plant height* (*average*).—1.79 m (5-year-old plants).

*Plant spread* (*average*).—2.09 m (5-year-old plants).

*Flowers bud density along flowering twigs* (*number during January*).—High.

*Twigginess*.—Medium-low.

*Tendency toward evergreenness*.—Medium-low.

*Productivity* (*when hand-harvested in northeast Florida*).—3.5 kg/season (5-year-old plants).

*Chilling requirement*.—150 hours below 7° C.

*Cold hardiness*.—Has been grown in temperate climates with extremely cold winter temperatures. Plants have survived winter freezes of −7° C. with minimal damage.

*Ease of propagation*.—Has only been propagated from softwood stem cuttings, where the rooting percentage is greater than 90% and comparable to other varieties.

Trunk and branches:

*Suckering tendency*.—Low.

*Surface texture*.—Strong 12-month-old shoots (observed May of 2020): smooth. Surface texture (of 3 year-old and older wood) — rough.

*Color*.—Color of new twigs observed in the field: R.H.S. 6th Ed. Fan 3 Yellow-green group 145 strong yellow-green A. Color of 3 year-old, rough textured canes: R.H.S. 6th Ed. Fan 4 Greyed-Green group 197 Greyish yellow-green D.

*Average internode length* (*strong, upright shoots measured in June*).—19.41 mm.

Petiole:

*Length*.—5.12 mm.

*Width*.—1.82 mm.

*Color*.—R.H.S. 6th Ed. Fan 3 Yellow Green Group 145 Light Yellow Green C.

*Texture*.—Smooth with presence of pubescence along the sides and back of the petiole.

Leaves:

*Length* (*average*).—6.06 cm.

*Width* (*average*).—3.15 cm.

*Petiole length* (*average*).—0.51 cm.

*Petiole diameter* (*average*).—0.18 cm.

*Shape*.—Elliptic.

*Leaf base*.—Elliptic.

*Leaf apex*.—Acute.

*Margin*.—Entire.

*Surface color*.—Upper: R.H.S. 6$^{th}$ Ed. Fan 3 Green Group NN137 Greyish Olive-Green A. Lower: R.H.S. 6$^{th}$ Edition Fan 3 Green group N138 Pale Green C.

*Pubescence*.—Upper and lower surfaces and margins: Absent at all.

*Timing of vegetative bud burst* (*early, medium, late*).—Medium.

*Relative time of leafing versus flowering* (*without mid-winter hydrogen cyanamide treatment*).—Leafing occurs after flowering.

Flowers:

*Arrangement*.—Alternately along a short leafless deciduous branch.

*Fragrance*.—very slight floral fragrance.

*Shape*.—Urceolate, cylindrical.

*Flowering period*.—50% anthesis was observed Jan. 13, 2020, Waldo, Fla. Stage IV 2014 Block (5 yr old Plants).

*Cluster*.—Medium.

*Number of flowers per cluster* (*average*).—5.2.

*Pedicel*.—Length at time of anthesis (average): 4.93 mm. Color at time of anthesis: R.H.S. 6$^{th}$ Ed. Fan 3 Yellow-Green Group 145 Light Yellow-Green B on non-sun exposed side with (Partially) R.H.S. 6$^{th}$ Ed. Fan 3 Yellow-Green Group 145 Light Yellow Green B and (partially) R.H.S. 6$^{th}$ Ed. Fan 4 Greyed-Purple 185 Moderate Red B on the sun exposed side.

*Peduncle*.—Length at time of anthesis (average): 15.02 mm. Color at time of anthesis: R.H.S. 6th Ed. Fan 3Yellow-Green Group 145 Light Yellow-Green B with (partially) R.H.S. 6th Ed. Fan 3 Yellow-Green Group 145 Light Yellow-Green B and (partially) R.H.S. 6th Ed. Fan 2 Red Purple Group 63 Strong Purplish Red A on sun exposed side.

*Calyx*.—Surface texture: Smooth. Diameter (average): 4.99 mm. Color (outer surface, visible at the time of anthesis without removing the corolla tube): R.H.S. 6$^{th}$ Ed. Fan 3 Yellow-Green Group 144 Strong Yellow Green A to R.H.S. 6$^{th}$ Ed. Fan 3 Yellow-Green Group 144 Strong Yellow-Green C on calyx lobes.

*Corolla*.—Diameter (average): 6.50 mm. Length (average, from pedicel attachment point to corolla tip excluding the pedicel): 9.18 mm. Aperture diameter (average): 2.80 mm. Texture: Smooth. Color: R.H.S.

6th Ed. Fan 4 Greyed-Yellow Group 160 Yellow D. Anthocyanin coloration in corolla tube: None detected.

Reproductive organs:

*Style*.—Length (average, top of ovary to stigma tip): 8.75 mm. Color: R.H.S. 6th Ed. Fan 3 Yellow-Green Group 145 Light Yellow Green C. Location of tip of stigma relative to tip of the corolla: 0.08 mm below the opening of the corolla tip.

*Anthers*.—Color: R.H.S. 6th Ed. Fan 4 Grey-Orange Group N167 Brownish Orange A. Pollen: Medium to High. Pollen germination: Greater than 90%. Color: R.H.S. 6th Ed. Fan 4 Greyed-Yellow Group 160 Pale Yellow D. Filament length: 6.39 mm. Filament width: 1.00 mm.

*Self-fruitfulness*.—Low to medium. Planting in the field configurations that promote cross-fertilization with other southern highbush varieties is recommended.

Fruit:

*Mean date of 50% harvest in Citra, Fla*.—Between Week 15 and 16.

*Diameter of calyx aperture* (*average, mature berry*).—4.94 cm.

*Size and shape of calyx lobes* (*mature berry*).—Small calyx lobes that are erect to incurving with a moderate shallow calyx basin.

*Pedicel length* (*average, ripe berry*).—6.36 mm.

*Detachment force for ripe berries* (*easy, medium, hard*).—Easy.

*Fruit cluster density* (*sparse, medium, dense*).—Medium.

*Number of berries per cluster* (*average*).—3.48.

*Fruiting type*.—On one-year-old shoots and current season's shoots.

Berry:

*Cluster* (*tight, medium, loose*).—Medium.

*Weight* (*average, on well-pruned plants*).—Mean of 2.3 g.

*Height* (*average*).—1.33 cm.

*Width* (*average*).—1.72 cm.

*Shape*.—Oblate.

*Surface color of mature berries ripe on plant*.—R.H.S. 6thEd. Fan 2 Violet-Blue Group 97 Light Purplish-Blue B.

*Intensity of fruit bloom*.—Medium to High.

*Surface color of ripe berry after polishing*.—R.H.S. 6th Ed. Fan 4 Black Group 203 Bluish-Black C.

*Immature berry color*.—With bloom: R.H.S. 6th Ed. Fan 3 Yellow-Green Group 144 Light Yellow-Green D. Without bloom: R.H.S. 6th Ed. Fan 3 Yellow-Green Group N144 Strong Yellow-Green D.

*Flesh color*.—R.H.S. 6th Ed. Fan 3 Yellow-Green Group 150 Light Yellow-Green D.

*Surface wax*.—Surface wax on 'Sentinel' has medium surface wax persistence.

*Pedicel scar*.—Small and dry, with an average size of 1.63 mm.

*Firmness*.—Firm, with average of 197.5 g/mm.

*Flavor*.—Sweet, with low acidity.

*Intensity of fruit sweetness*.—Medium.

*Texture*.—Fleshy, Juicy, non-mealy texture, and no stone cells present.

*Fruit storage quality*.—Fruit is firm and can be stored without shriveling, mold or loss of firmness for 2 weeks at 4° C.

Seeds:

*Color of dried seeds*.—R.H.S. 6th Ed. Fan 4 Greyed-Orange Group N167 Brownish Orange B.

*Weight of well-developed dried seeds*.—Mean of 0.50 mg.

*Length of well-developed dried seeds*.—Mean of 1.83 mm.

*Width of well-developed dried seeds*.—Mean of 0.99 mm.

Use: Produces southern highbush blueberries suitable for hand harvest for the fresh fruit markets.

Resistance to diseases, insects, and mites: Has grown vigorously and shows good bush survival in the field, with almost no young plants dying soon after planting. Reaction to the various fungal species that cause summer leaf spots (including rust) is lower than those of other southern highbush varieties. Fungicide applications may be needed after harvest to reduce foliar diseases and retain leaves into the fall for maximum flower bud set. Appears to be more tolerant than other southern highbush varieties to spider mites. Susceptibility to typical blueberry insect and mite pathogens such as spotted wing drosophila (*Drosophila suzukii*), blueberry gall midge (*Dasineura oxycoccana*), blueberry flower thrips (*Frankliniella* spp), and blueberry bud mite (*Acalitus vaccini*) appear similar to other southern highbush cultivars.

What is claimed is:

1. A new and distinct variety of southern highbush blueberry plant named 'Sentinel', as illustrated and described herein.

* * * * *